United States Patent [19]

Steer

[11] Patent Number: 4,559,048
[45] Date of Patent: Dec. 17, 1985

[54] COUPLING FOR AN OSTOMY BAG

[75] Inventor: Peter L. Steer, Surrey, England

[73] Assignee: Craig Medical Products Limited, Sussex, England

[21] Appl. No.: 624,321

[22] Filed: Jun. 25, 1984

[30] Foreign Application Priority Data

Jul. 1, 1983 [GB] United Kingdom ............. 8317889

[51] Int. Cl.⁴ ............................................. A61F 5/44
[52] U.S. Cl. ................................. 604/338; 604/339
[58] Field of Search .............................. 604/332-345

[56] References Cited

U.S. PATENT DOCUMENTS

| 4,213,458 | 7/1980 | Nolan et al. | 128/283 |
| 4,232,672 | 11/1980 | Steer et al. | 604/336 |
| 4,419,100 | 12/1983 | Alexander | 604/339 |
| 4,460,363 | 7/1984 | Steer et al. | 604/342 |

FOREIGN PATENT DOCUMENTS

| 0089138 | 9/1983 | European Pat. Off. |
| 0098718 | 1/1984 | European Pat. Off. |
| 1021145 | 3/1966 | United Kingdom . |
| 1099455 | 1/1968 | United Kingdom . |
| 1568860 | 6/1980 | United Kingdom . |
| 1571657 | 7/1980 | United Kingdom . |
| 1579875 | 11/1980 | United Kingdom . |
| 1583027 | 1/1981 | United Kingdom . |
| 1586823 | 3/1981 | United Kingdom . |
| 1586824 | 3/1981 | United Kingdom . |
| 2119654 | 11/1983 | United Kingdom . |

Primary Examiner—William R. Dixon, Jr.
Assistant Examiner—Karl Group
Attorney, Agent, or Firm—L. S. Levinson; R. E. Lee, Jr.

[57] ABSTRACT

A coupling for joining a pad or dressing to an ostomy bag includes coupling elements each of closed loop form, usually circular to define a stoma aperture therein, the body side element being constructed so that it can be fixed to the pad or dressing and the bag side element being constructed so that it can be fixed to one wall of an ostomy bag. The body side element includes an inner wall which continuously encircles the aperture and a series of projecting members uniformly radially spaced from the inner wall and located in an array which surrounds the inner wall. The bag side element includes a rib member encircling the aperture for making sealing engagement, when the coupling elements are joined, with the outer surface of the inner wall. The coupling also has an annual ring which is constructed to be snap-fitted to the body side coupling element to extend radially outwardly therefrom. In use, the wearer places his thumbs under the ring to support the body side coupling element against the inwardly-directed force applied when fitting a new bag.

14 Claims, 6 Drawing Figures

U.S. Patent  Dec. 17, 1985  4,559,048
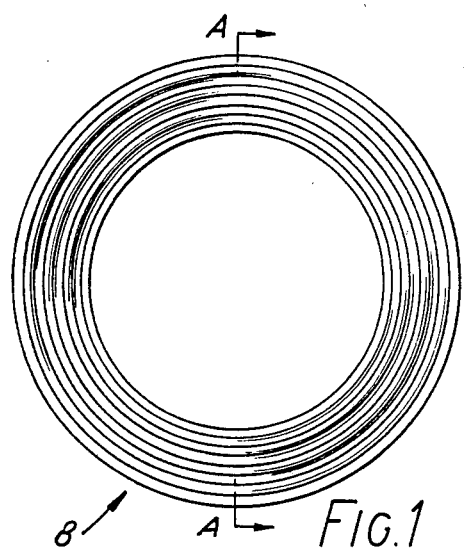
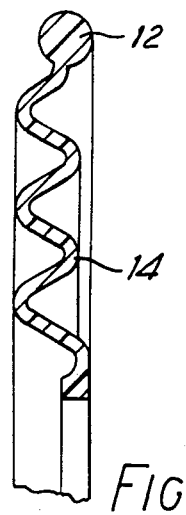
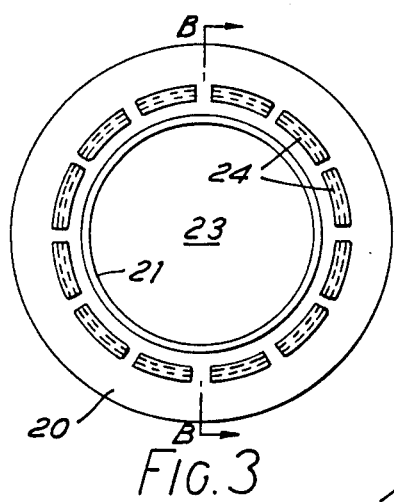
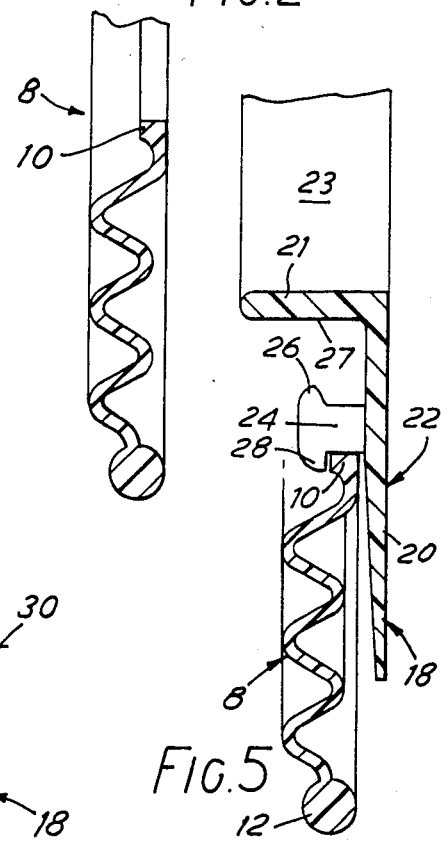
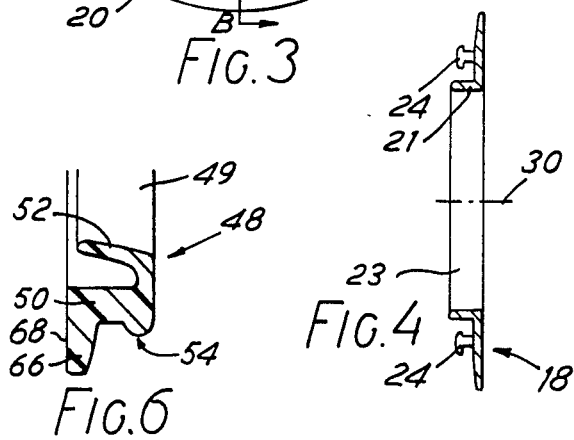

COUPLING FOR AN OSTOMY BAG

BACKGROUND OF THE INVENTION

This invention relates to a coupling for joining an ostomy bag to a pad or surgical dressing. Ostomy bags are usually secured to a pad or surgical dressing which contacts the user's skin and surrounds the stoma. There is a need for a coupling between pad and bag which allows the bag to be readily removed when necessary, and replaced by a clean, empty bag. At the same time, it is essential that the coupling should be a secure one, and prevent leakage particularly of liquids and gases.

Efforts have been made, see for example the proposal in British Patent Specification No. 1 021 145 published in 1966, to provide a connector whereby the bag can be readily removed and replaced. But this arrangement involves two separate operations, firstly one must unscrew the connector which carries the bag from the connector which is secured to the body and this involves a risk of leakage as it is necessary to invert the bag. Also it is an awkward operation. It will be appreciated that at this time the bag is full or partly-full of bodily waste products, and manipulation of the coupling will be an unpleasant operation even if, as is often not the case, the user has a high degree of dexterity.

British Patent Specification No. 1 009 455 discloses an appliance in which one ring co-operates with a second part-ring which is used to trap the neck of a bag when the two rings are inter-engaged with the bag mouth between them. If adequate security against leakage is to be provided, it is necessary that the two rings should be a tight fit; however, this makes it difficult for the user to pull off the part-ring and it is especially difficult for a user who is old or infirm. As the part-ring is pulled off, there is the probability that the security of attachment of the first ring to the surgical dressing, or of the dressing to the skin of the wearer will be impaired. This may also cause discomfort to the wearer.

A more recent proposal, which has enjoyed wide commercial success is described and claimed in British Pat. No. 1 571 657. The reader is also referred to British Patent Specifications Nos. 1 568 850; 1 579 875; 1 583 823 and 1 586 824. It is desirable to have a coupling for an ostomy bag which is flexible, which has the features of easy fitting and unfitting and good security of attachment and sealing, and which also has a flatter design, that is to say the coupling does not project so far outwardly from the body of the wearer, than the coupling disclosed and illustrated in Pat. No. 1 571 657.

A satisfactory ostomy bag coupling should be easy for the wearer to attach. Current designs are less than ideal in this respect. Coupling is made difficult by the desire of the designer to ensure a good seal between the two coupling elements which means that they are constructed as a tight fit one into the other, and by the fact that the wearer is attempting to apply the bag side coupling element to the body side coupling element by pushing the former forwards from the latter. However, as the stoma end and region of the stoma is tender, it is painful to the wearer if any significant portion of the considerable pushing force applied to the bag side element in coupling it to the body side element is transmitted to the body of the wearer. Only a few of the present designs of ostomy bag coupling elements known to the Applicant attempt to address this problem, and in the Applicant's belief none have solved it satisfactorily.

SUMMARY OF THE INVENTION

According to the present invention, there is provided a coupling for joining a pad or dressing to an ostomy bag including first and second coupling elements each of closed loop form to define a stoma aperture therein, the first (body side) element being constructed so that it can be fixed to the pad or dressing and the second (bag side) element being constructed so that it can be fixed to one wall of an ostomy bag, in which the first element includes an inner wall which continuously encircles the aperture and a series of projecting members uniformly radially spaced from the inner wall and located in an array which surrounds the inner wall, and in which the second element includes a rib member encircling the aperture for making sealing engagement, when the coupling elements are joined, with the outer surface of the inner wall, the coupling also having an annular ring which is constructed to be snap-fitted to the body side coupling element to extend radially outwardly therefrom.

Such an annular ring has a radial dimension such that the wearer can place fingers or thumbs behind the ring, that is between the ring and his(her) body to support the body side coupling element against the inwardly-directed force applied when coupling the two elements together to attach the bag to the pad. The ring is preferably made of plastics material and may have a peripheral bead of rounded shape, that is to say a peripheral bead which is largely circular seen in cross-section. The body side coupling element preferably has outwardly projecting latches integral with at least some of the projecting members and the annular ring in use is snapped over these latches: in this way it is securely attached to the body side coupling element. The annular ring preferably consists of an undulating web portion connecting the peripheral bead with an inner ring portion. The latter may have a substantially rectangular cross-section.

The rib member of the bag side coupling element preferably has a deflectible sealing skirt extending therefrom, which when the coupling elements are joined, engages the outer surface of the inner wall.

According to an advantageous feature of the invention, the projections take the form of arcuate ribs, each having an inwardly-facing hook portion. The outer surface of the rib member may advantageously have a latch or "step" formation to retain the ring. The latch formation may be of substantially right angle shape as seen in vertical axial cross-section.

BRIEF DESCRIPTION OF THE DRAWINGS

The invention will be better understood from the following non-limiting description of an example thereof given with reference to the accompanying drawings in which:

FIG. 1 is a planar view of one example of an annular ring for use in a coupling according to the invention;

FIG. 2 is an enlarged cross-section on the line A—A of FIG. 1;

FIG. 3 is a planar view of one example of a body side coupling element for use in a coupling according to the invention;

FIG. 4 is a cross-section on the line B—B of FIG. 3;

FIG. 5 is an enlarged cross-sectional view of a portion of the body side coupling element of FIG. 4 in assembled condition with a portion of the ring of FIG. 2.

FIG. 6 is an enlarged cross-sectional view of a portion of one example of a bag side coupling element for use with the body side coupling elements of FIGS. 3, 4 and 5.

DETAILED DESCRIPTION OF THE DRAWINGS

In this specification, the words "front" and "rear" are used in relation to a coupling as worn by a wearer, that is to say, the "front" element of such a coupling is the element attached to the bag and the "rear" element is that attached to the pad.

The annular ring 8 for an ostomy bag coupling illustrated in FIG. 1 and 2 has an inner ring portion 10 which is shown with substantially rectangular cross-section. This is joined to a peripheral bead 12 by an undulating web portion 14. The ring is preferably made of a synthetic plastics material. One suitable material is polymerised ethylene vinyl acetate (E.V.A.) such as E.V.A. grade 502.

One example of a body side coupling element according to the invention is illustrated in FIGS. 3–5. The body side coupling element 18 has a flange 20 whose surface 22 is attached to a pad or dressing, not shown. The pad has a central stoma aperture, in the conventional manner (see for example British Pat. No. 1 571 657). The element 18 has an inner peripheral wall 21 encircling a stoma aperture 23. Surrounding the wall 21 are a plurality of spaced projections 24. These are uniformly radially spaced from the wall 21, and at least some of them (and preferably all of them) have radially inwardly extending hook portions 26. Also at least some (and preferably all) of the projections 24 have radially outwardly extending latch portions 28.

FIG. 6 shows an enlarged cross-sectional view of a portion of one example of a bag side coupling element 48 suitable for use with the body side coupling element 18 of FIGS. 3–5. The bag side coupling element 48, like the body side coupling element 18, is of closed loop form defining an aperture 49 to receive the stoma of the wearer. The element 48 includes rib member 50 encircling the aperture 49, the rib member 50 being integral with a deflectable sealing skirt 52 located on the radially inner side of the rib 50 and with a step formation 54 located on the radially outer side of the rib 50.

The bag side element 48 also includes a lateral flange 66 whose surface 68 is secured in any convenient manner, for example, by adhesive, to one wall of an ostomy bag, not shown.

In the manner described in U.S. patent application Ser. No. 8,207,172 dated Mar. 11, 1982, the hook portions 26 of the body side coupling element 18 cooperate with the step formation 54 on the bag side coupling element 48 to firmly attach the two coupling elements together. The deflectable sealing skirt 52 contacts the surface 27 of wall 21 to provide a seal.

Referring to FIG. 5, when the coupling is first assembled, the ring 8 is snap-fitted over the projections 24 and is held thereon by the latch portions 28 acting on the inner ring portion 10 of ring 8. The inherent flexibility of the synthetic plastics used is chosen to permit the necessary small deformation of the projections 24 to occur, and these projections spring back outwardly after the ring 8 has been forced over them.

The array of projections 24 may for example be made up of a plurality of arcuate ribs, e.g. 12 in number, each of which is spaced from its neighbor by a space whose length measured around the periphery is form 1/10 to ½ of the peripheral length of each arcuate rib. Each arcuate rib may have a hook portion defined by a smoothly curved surface and a straight hooking surface as seen in vertical axial cross-section. The hooking surface may be at an angle from 50° to 70°, preferably 60°, to the axis of the coupling.

As stated, the body side and bag side coupling elements 18 and 48, respectively, are of closed loop form and define apertures intended to receive the stoma of the wearer. While these apertures have been illustrated as circular, there is no reason why they should not be elliptical or of other shape; however, a circular configuration has been found to be satisfactory. These coupling elements may each be integrally molded from a moldable synthetic plastics material. One example of a suitable material is that known as "E.V.A." (polymerized ethylene vinyl acetate). Other synthetic plastics materials may be suitable.

The surface 22 of the body side coupling element 18 of the flange is intended to be secured, for example by adhesive, to a surface of a pad or dressing such as a pad of the material known as "Dermahesive" (registered trademark). Such a pad or circular dressing would have a similar circular aperture to the aperture 23 and would have an opposite surface which contacts and adheres to the skin of the person wearing the ostomy bag. Other kinds of pad or dressing could be employed, for example those based on Karaya gum compositions.

The inner wall 21 completely encircles the stoma aperture 23, and, as illustrated, the series of projecting members 24 are secured to or integral with the flange 20, spaced from one another in a peripheral direction, and radially-spaced from the inner wall 21. In other words, these projecting members are disposed in a circular array which surrounds the inner wall 21. In conjunction with the inner wall 21 they define a space which, when the coupling is connected, is occupied by a rib member 50 of the bag side coupling. Each projecting member 24 is arcuate (see FIG. 3) and each has an inwardly-facing hook portion 26. This may extend along the whole peripheral length of each arcuate projection 24. Each arcuate projection 24 may have its hook portion defined by a smoothly curved surface and a straight hooking surface.

I claim:

1. A coupling for joining a pad or dressing to an ostomy bag including first and second coupling elements each of closed loop form to define a stoma aperture therein, the first element being constructed so that it can be fixed to the pad or dressing and the second element being constructed so that it can be fixed to one wall of an ostomy bag, in which the first element includes an inner wall which continuously encircles the aperature and a series of projecting members uniformly radially spaced from the inner wall and located in an array which surrounds the inner wall, and in which the second element includes a rib member encircling the aperture for making sealing engagement, when the coupling elements are joined, with the outer surface of the inner wall, the coupling also having as a third element an annular ring which is constructed to be snap-fitted to the body side coupling element to extend radially outwardly therefrom whereby a wearer can place thumbs between the ring and body to support the first coupling element against the inwardly-directed force applied when coupling the first and second coupling elements together to attach the bag to the pad.

2. A coupling according to claim 1 in which the first coupling element comprises outwardly projecting latches integral with at least some of the projecting members and the annular ring is snapped over these latches whereby it is securely attached to the first coupling element.

3. A coupling according to claim 2 in which the ring is made of plastics material and comprises a peripheral bead of rounded shape.

4. A coupling according to claim 3 in which the annular ring comprises an undulating web portion connecting the peripheral bead with an inner ring portion.

5. A coupling according to claim 4 in which the inner ring portion comprises substantially rectangular cross-section.

6. A coupling according to claim 2 in which the rib member of the second coupling element has a deflectible sealing skirt extending therefrom, which, when the first and second coupling elements are joined, engages the outer surface of the inner wall.

7. A coupling according to claim 6 in which the projecting members take the form of arcuate ribs, each having an inwardly-facing hook portion for engaging a portion of the rib member.

8. A coupling for joining a pad or dressing to an ostomy bag including first and second coupling elements each of closed loop form to define a stoma aperture therein, the first element being constructed so that it can be fixed to the pad or dressing and the second element being constructed so that it can be fixed to one wall of an ostomy bag, in which the first element includes an inner wall which continuously encircles the aperature and a projecting member radially spaced from the inner wall and which surrounds the inner wall, and in which the second element includes a rib member encircling the aperture for making sealing engagement, when the coupling elements are joined, with the outer surface of the inner wall, the coupling also having as a third element an annular ring which is constructed to the snap-fitted to the body side coupling element to extend radially outwardly therefrom whereby a wearer can place thumbs between the ring and body to support the first coupling element against the inwardly-directed force applied when coupling the first and second coupling elements together to attach the bag to the pad.

9. A coupling according to claim 8 in which the first coupling element has an outwardly projecting latch portion integral with the projecting member and the annular ring is snapped over the latch portion whereby it is securely attached to the first coupling element.

10. A coupling according to claim 9 in which the ring is made of plastics material and has a peripheral bead of rounded shape.

11. A coupling according to claim 10 in which the annular ring comprises an undulating web portion connecting the peripheral bead with an inner ring portion.

12. A coupling according to claim 11 in which the inner ring portion comprises a substantially rectangular cross-section.

13. A coupling according to claim 9 in which the rib member of the second coupling element has a deflectible sealing skirt extending therefrom, which, when the coupling elements are joined, engages the outer surface of the inner wall.

14. A coupling according to claim 13 in which the projecting member takes the form of an arcuate rib having an inwardly-facing hook portion for engaging a portion of the rib member.

* * * * *